(12) United States Patent
Saito et al.

(10) Patent No.: US 12,007,387 B2
(45) Date of Patent: Jun. 11, 2024

(54) ANALYSIS THRESHOLD GENERATION DEVICE AND ANALYSIS THRESHOLD GENERATION METHOD

(71) Applicant: JVCKENWOOD Corporation, Yokohama (JP)

(72) Inventors: Atsushi Saito, Yokohama (JP); Makoto Itonaga, Yokohama (JP); Masayuki Ono, Yokohama (JP); Shigehiko Iwama, Yokohama (JP); Masahiro Yamamoto, Yokohama (JP)

(73) Assignee: JVCKENWOOD CORPORATION, Yokohama (JP)

( * ) Notice: Subject to any disclaimer, the term of this patent is extended or adjusted under 35 U.S.C. 154(b) by 771 days.

(21) Appl. No.: 17/111,874

(22) Filed: Dec. 4, 2020

(65) Prior Publication Data

US 2021/0088508 A1   Mar. 25, 2021

Related U.S. Application Data

(63) Continuation of application No. PCT/JP2019/020060, filed on May 21, 2019.

(30) Foreign Application Priority Data

Jun. 6, 2018   (JP) ................... 2018-108514

(51) Int. Cl.
| | | |
|---|---|---|
| G01N 33/543 | (2006.01) | |
| G01N 21/25 | (2006.01) | |
| G01N 21/41 | (2006.01) | |

(52) U.S. Cl.
CPC ......... *G01N 33/543* (2013.01); *G01N 21/255* (2013.01); *G01N 21/41* (2013.01)

(58) Field of Classification Search
CPC .......... B01L 2300/0654; G01N 21/255; G01N 33/543; G01N 21/44
See application file for complete search history.

(56) References Cited

U.S. PATENT DOCUMENTS

| | | | |
|---|---|---|---|
| 2009/0071225 A1* | 3/2009 | Schilffarth ......... | G01N 15/0205 73/1.02 |
| 2010/0271620 A1* | 10/2010 | Goebel .............. | G01N 15/1459 356/73 |

(Continued)

FOREIGN PATENT DOCUMENTS

| | | |
|---|---|---|
| JP | 5-5741 A | 1/1993 |
| JP | 8-62274 A | 3/1996 |

(Continued)

OTHER PUBLICATIONS

Extended European search report dated Jul. 19, 2021 issued in corresponding European Application No. 19814025.3.

*Primary Examiner* — Brian J. Sines
(74) *Attorney, Agent, or Firm* — Nath, Goldberg & Meyer; Jerald L. Meyer

(57) ABSTRACT

An analysis threshold generation device includes a threshold calculation unit for generating a pair of thresholds for a pulse width of a pulse included in a light reception level signal or a pair of thresholds for a pulse amplitude of the pulse. The analysis threshold generation device includes a threshold correction unit for generating a pair of thresholds used for analysis in accordance with the pair of thresholds generated by the threshold calculation unit and a count value output from a pulse count unit. The threshold calculation unit repeatedly generates a new pair of thresholds in which at least one of the pair of thresholds is changed every time the pulse count unit counts the pulse until reaching a predetermined value.

6 Claims, 9 Drawing Sheets

(56) References Cited

U.S. PATENT DOCUMENTS

2017/0074776 A1 3/2017 Fox
2017/0082530 A1* 3/2017 Sieracki ............ G01N 15/1429

FOREIGN PATENT DOCUMENTS

| JP | 2002-530786 A | 9/2002 |
| JP | 2010-109195 A | 5/2010 |
| JP | 2016-70782 A | 5/2016 |

* cited by examiner

FIG. 7

| VL | COUNT VALUE |
|---|---|
| 0 | Count (0) |
| 1 | Count (1) |
| 2 | Count (2) |
| ⋮ | ⋮ |
| $V_n$ | Count ($V_n$) |
| $V_{n+1}$ | Count ($V_{n+1}$) |
| ⋮ | ⋮ |
| $V_{max}$ | Count ($V_{max}$) |

ANALYSIS THRESHOLD GENERATION DEVICE AND ANALYSIS THRESHOLD GENERATION METHOD

CROSS REFERENCE TO RELATED APPLICATION

This application is a Continuation of PCT Application No. PCT/JP2019/020060, filed on May 21, 2019, and claims the priority of Japanese Patent Application No, 2018-108514, filed on Jun. 6, 2018, the entire contents of both of which are incorporated herein by reference.

BACKGROUND

The present disclosure relates to an analysis threshold generation device and an analysis threshold generation method. More particularly, the present disclosure relates to an analysis threshold generation device and an analysis threshold generation method for analyzing biomaterials such as antigens and antibodies.

Immunoassays are known that quantitatively analyze disease detection and therapeutic effects by detecting particular antigens or antibodies associated with diseases as biomarkers. One of the immunoassays is an enzyme-linked immunosorbent assay (ELISA) for detecting antigens or antibodies labeled by enzymes, which is widely used because of having the advantage of low costs.

The ELISA requires a long time, such as several hours to a day, for completing an analyzing process including pre-treatment, antigen-antibody reaction, bond/free (B/F) separation, and enzyme reaction. To deal with this problem, a technology is disclosed in which antibodies fixed to an optical disc are allowed to bind to antigens in a specimen, and the antigens are further bound to particles provided with antibodies and scanned with an optical head, so as to count the particles captured on the optical disc in a short period of time (refer to Japanese Unexamined Patent Application Publication No. H05-5741). Another technology is disclosed in which biosamples and particles are caused to adhere to a surface of an optical disc having a tracking structure so as to detect a change in signal by an optical pickup (refer to Japanese Translation of PCT International Application Publication No. 2002-530786).

SUMMARY

Using pulses included in reflection signals from the optical disc enables the count of particles adhering to the optical disc. In this case, since pulses derived from noise are also included, predetermined conditions are assigned to a pulse amplitude and a pulse width to selectively count pulses derived from the particles, so as to count detection target substances bound to the particles.

Constantly setting the conditions regarding the pulse amplitude and the pulse width for determining the pulses derived from the particles, however, may lead the analysis of the same sample to different results to fluctuate the counting results, decreasing the accuracy of the analysis.

An analysis threshold generation device according to an aspect of the present disclosure includes an optical pickup configured to irradiate an analysis substrate with an irradiation light and receive a reflection light of the irradiation light from the analysis substrate to generate a light reception level signal. The analysis substrate has a surface to which a detection target substance and a particle bound to the detection target substance are fixed. The analysis threshold generation device includes a threshold calculation unit configured to generate a pair of thresholds for a pulse width of a pulse included in the light reception level signal or a pair of thresholds for a pulse amplitude of the pulse. The analysis threshold generation device includes a pulse determination unit configured to determine whether the pulse width is present within a range of the pair of thresholds for the pulse width or determine whether the pulse amplitude is present within a range of the pair of thresholds for the pulse amplitude. The analysis threshold generation device includes a pulse count unit configured to count the pulse determined to be present within the range of the generated pair of thresholds by the pulse determination unit, and output a count value of the pulse counted. The analysis threshold generation device includes a threshold correction unit configured to generate a pair of thresholds used for analysis in accordance with the pair of thresholds generated by the threshold calculation unit and the count value output from the pulse count unit. The threshold calculation unit repeatedly generates a new pair of thresholds in which at least one of the pair of thresholds is changed every time the pulse count unit counts the pulse until reaching a predetermined value.

An analysis threshold generation method according to an aspect of the present disclosure includes an irradiation step of irradiating, with an irradiation light, an analysis substrate having a surface to which a detection target substance and a particle bound to the detection target substance are fixed. The analysis threshold generation method includes a signal generation step of receiving a reflection light of the irradiation light from the analysis substrate to generate a light reception level signal. The analysis threshold generation method includes a determination step of determining whether a pulse included in the light reception level signal is present within a range of a pair of thresholds set for a pulse width or determining whether the pulse is present within a range of a pair of thresholds set for a pulse amplitude. The analysis threshold generation method includes a count value output step of counting the pulse determined to be present within the range of the set pair of thresholds in the determination step, and outputting a count value of the pulse counted. The analysis threshold generation method includes a first threshold generation step of repeatedly generating a new pair of thresholds in which at least one of the pair of thresholds is changed every time the count value output step counts the pulse until reaching a predetermined value. The analysis threshold generation method includes a second threshold generation step of generating a pair of thresholds used for analysis in accordance with each pair of thresholds generated and the count value output in the count value Output step.

BRIEF DESCRIPTION OF THE DRAWINGS

FIG. 7 is a diagram showing an example of a count table according to the present embodiment.

DETAILED DESCRIPTION

Figure 1:
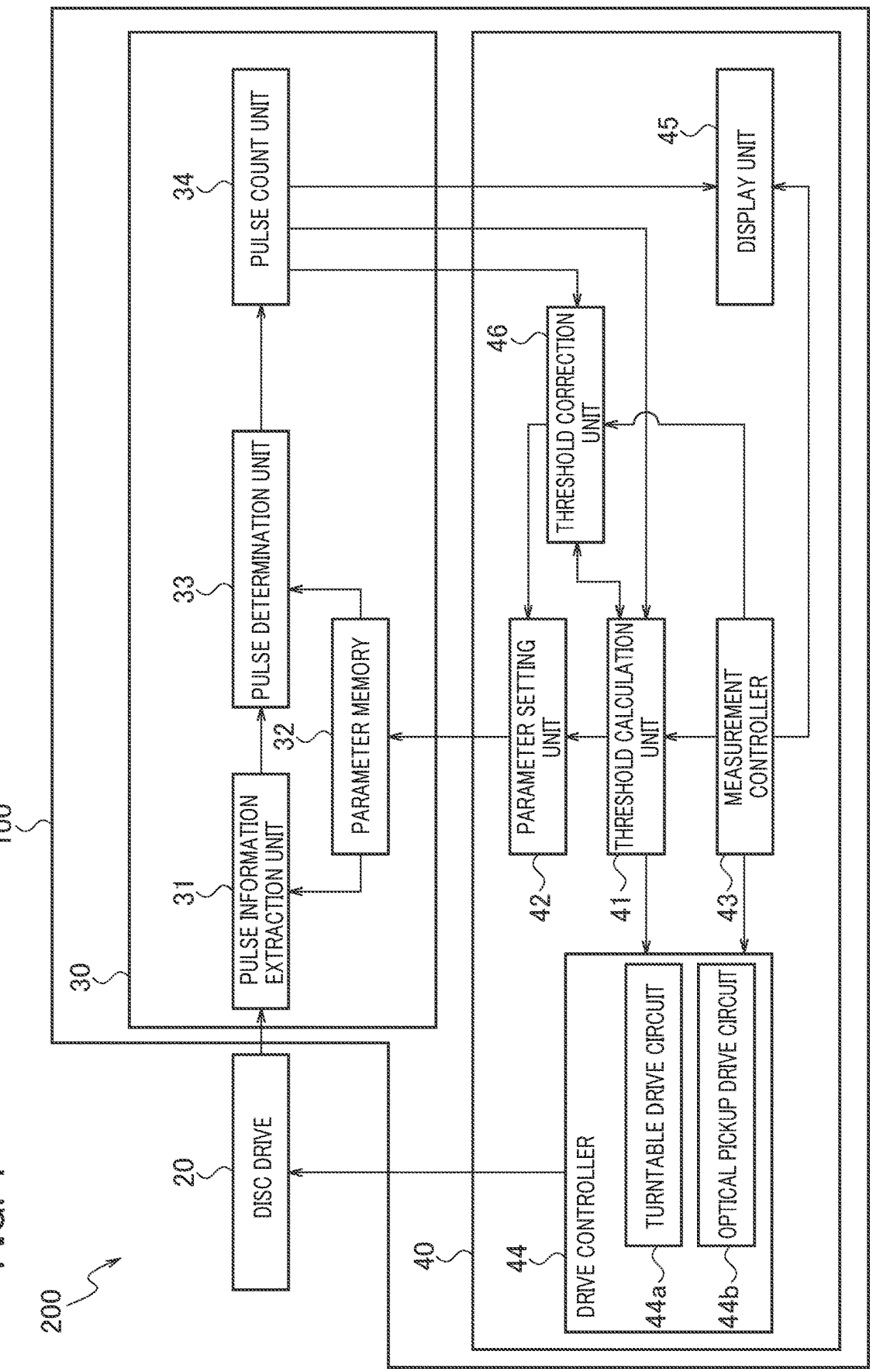
FIG. 1 is a block diagram showing a configuration of an analysis device including an analysis threshold generation device according to a first embodiment.

An analysis threshold generation device and an analysis threshold generation method according to the present embodiment are described below. The dimensions of the elements in the drawings are exaggerated for illustration purposes, and are not necessarily drawn to scale.

First Embodiment

An analysis threshold generation device and an analysis threshold generation method according to a first embodiment are described in detail below.

As shown in FIG. 1, the analysis threshold generation device 100 according to the present embodiment includes a pulse detection circuit 30 and a system controller 40. The present embodiment is illustrated below with an analysis device 200 including the analysis threshold generation device 100 and a disc drive 20, The disc drive 20 plays an analysis substrate 10. The analysis substrate 10 has a disc-like shape equivalent to optical discs such as Blu-ray discs (BDs), DVDs, and compact discs (CDs). The analysis substrate 10 is formed of resin material, such as polycarbonate resin and cycloolefin polymer, used for common optical discs. The analysis substrate 10 is not limited to the optical discs described above, and may be any optical disc having other configurations or conforming to prescribed standards.

Figure 2:
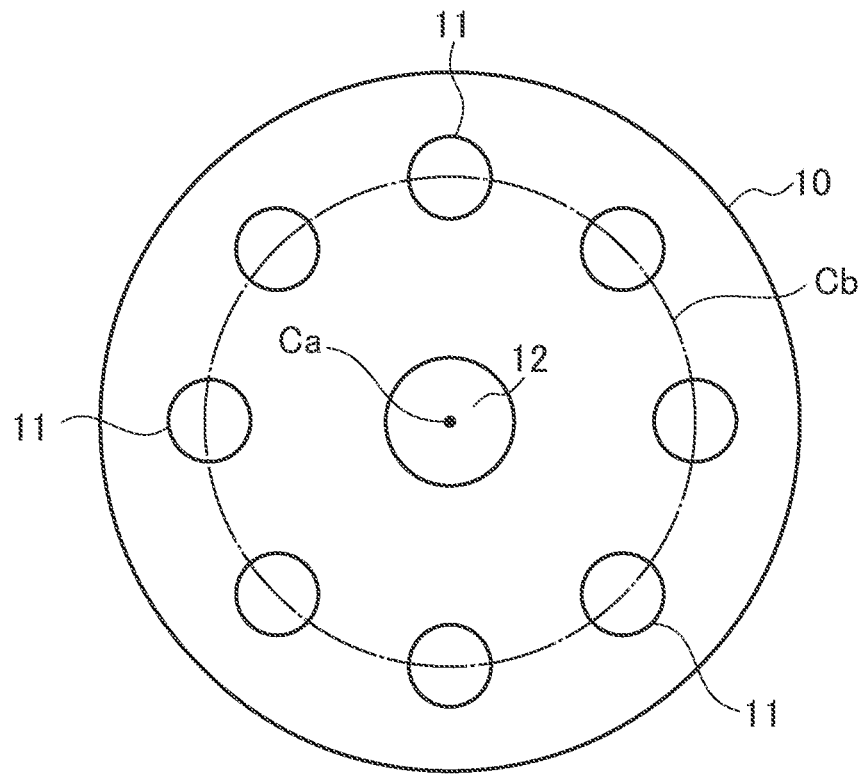
FIG. 2 is a top view showing an example of an analysis substrate having reaction regions.

As shown in FIG. 2, the analysis substrate 10 has reaction regions 11. The reaction regions 11 are regions as a target to be analyzed to which detection target substances 13, particles 14, and antibodies 15 and the like are fixed (refer to FIG. 4). According to the present embodiment, the analysis substrate 10 has a positioning hole 12 in the middle, and the eight reaction regions 11 are arranged at regular intervals such that the respective center points are located on the common circle Cb with respect to the center Ca of the analysis substrate 10. The number or the arrangement positions of the reaction regions 11 are not limited to this illustration.

Figure 3:
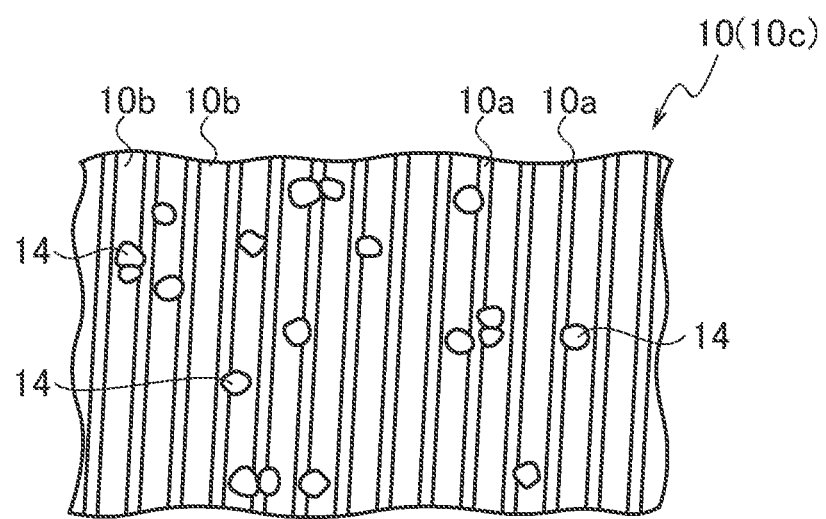
FIG. 3 is an enlarged top view showing a state in which particles are captured on a track region of a reaction region.

As shown in FIG. 3, the surface of the analysis substrate 10 is provided with track regions 10c having convex portions 10a and recesses 10b alternately arranged in a radial direction. The convex portions 10a and the recesses 10b are formed in a spiral from the inner circumference to the outer circumference of the analysis substrate 10. The convex portions 10a correspond to lands of an optical disc. The recesses 10b correspond to grooves of an optical disc. A track pitch of the recesses 10b which is a pitch in the radial direction is 320 nm, for example.

Figure 4:
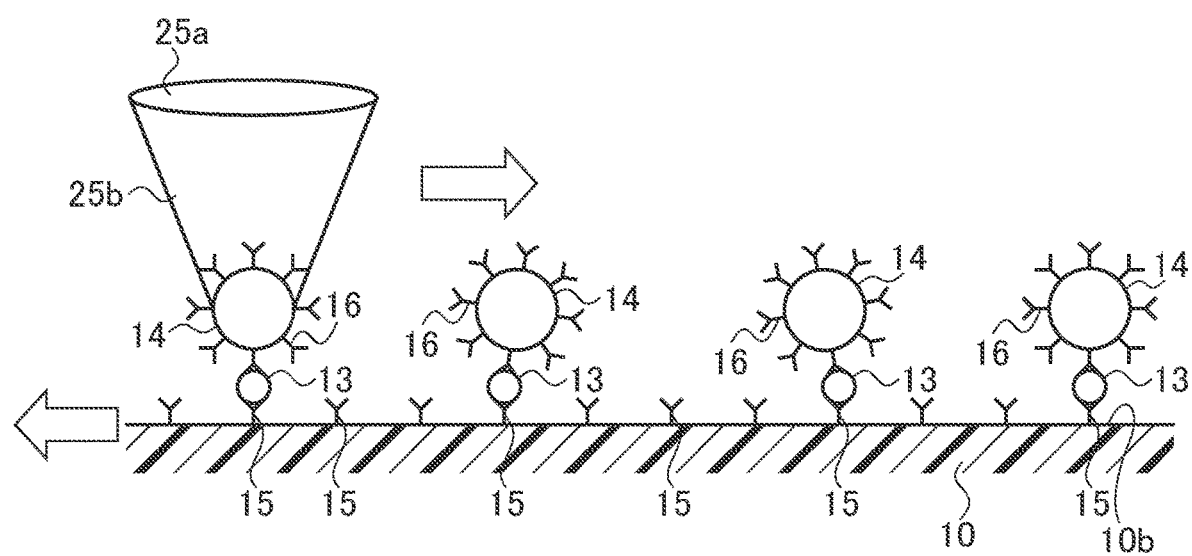
FIG. 4 is a schematic cross-sectional view showing a state in which detection target substances are captured and sandwiched between antibodies and particles in a recess of a track region.

As shown in FIG. 3 and FIG. 4, the detection target substances 13 and the particles 14 bound to the detection target substances 13 are fixed to the surface of the analysis substrate 10. In addition, antibodies 15 specifically binding to the detection target substances 13 are fixed to the surface of the analysis substrate 10. The antibodies 15 recognize and bind to the detection target substances 13 so that the detection target substances 13 are captured on the surface of the analysis substrate 10. The particles 14 are provided with a plurality of antibodies 16 recognizing the detection target substances 13, and are bound to the detection target substances 13 via the antibodies 16 so as to implement a sandwich structure.

The detection target substances 13 are antigens, such as specific protein, associated with diseases, for example. The use of such antigens as the detection target substances 13 contributes to the detection of diseases. For example, the detection target substances 13 such as exosomes vary in concentration in a body fluid depending on a condition of a particular disease as a target to be monitored, so as to serve as biomarkers. The size of the exosomes as the detection target substances 13 is about 100 nm.

The particles 14 serve as labels for the detection target substances 13. Examples of the particles 14 include, but are not limited to, labeling beads such as polymer particles, metallic particles, and silica particles. The particles 14 may be magnetic beads including magnetic material such as ferrite. The size of the particles 14 is about 200 nm.

Figure 5:
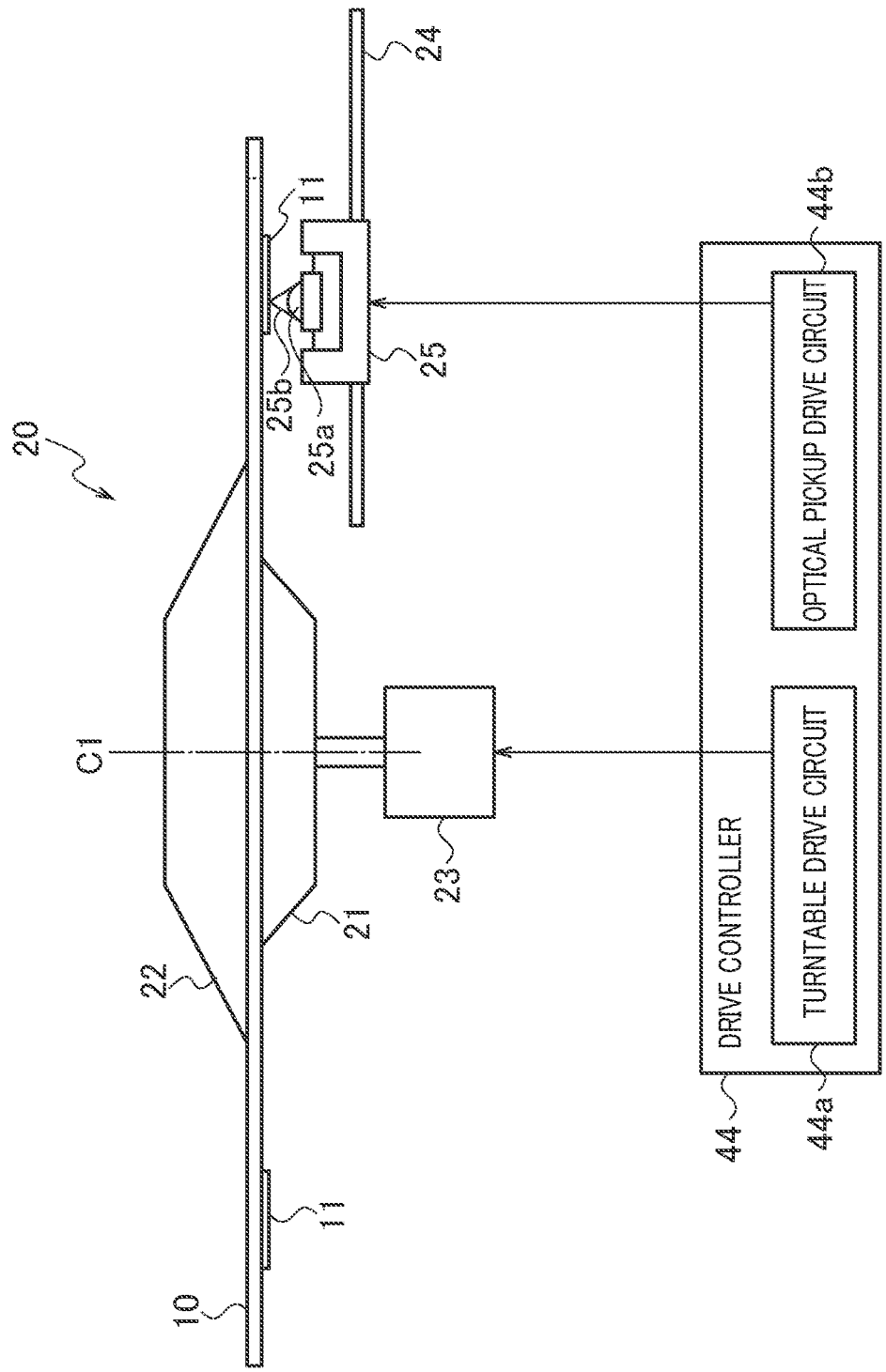
FIG. 5 is a schematic view showing an example of a disc drive according to the present embodiment.

As shown in FIG. 5, the disc drive 20 is an analysis substrate drive device including a turntable 21, a damper 22, a turntable drive unit 23, a guide shaft 24, and an optical pickup 25. The disc drive 20 may be a known information playing disc drive.

The analysis substrate 10 is placed on the turntable 21 with the surface provided with the reaction regions 11 facing down.

The damper 22 is driven in directions separating from and approaching the turntable 21, namely, in the upper and lower directions in FIG. 5. The analysis substrate 10 is held on the turntable 21 between the damper 22 and the turntable 21 when the damper 22 is driven in the lower direction. In particular, the analysis substrate 10 is held such that the center Ca of the analysis substrate 10 is located on the rotation axis C1 of the turntable 21.

The turntable drive unit 23 drives the turntable 21 to rotate about the rotation axis C1 together with the analysis substrate 10 and the damper 22. A spindle motor may be used as the turntable drive unit 23. The turntable drive unit 23 is controlled by a turntable drive circuit 44a of a drive controller 44.

The guide shaft 24 is placed in parallel to the analysis substrate 10 in the radial direction of the analysis substrate 10. The guide shaft 24 is arranged in a direction perpendicular to the rotation axis C1 of the turntable 21.

The optical pickup 25 is supported by the guide shaft 24. The optical pickup 25 is driven along the guide shaft 24 in the radial direction of the analysis substrate 10, which is perpendicular to the rotation axis C1 of the turntable 21, and parallel to the analysis substrate 10. The optical pickup 25 is controlled by an optical pickup drive circuit 44b of the drive controller 44.

The optical pickup 25 includes an objective lens 25a. The optical pickup 25 irradiates the analysis substrate 10 with irradiation light 25b. The irradiation light 25b is laser light, for example. The irradiation light 25b is condensed by the objective lens 25a on the surface of the analysis substrate 10. The optical pickup 25 is driven in the radial direction of the analysis substrate 10 which is rotating, so as to scan the recesses 10b with the irradiation light 25b.

The optical pickup 25 receives the reflection light of the irradiation light 25b from the analysis substrate 10 to generate a light reception level signal JS. As shown in FIG. 1, the optical pickup 25 outputs the light reception level signal JS to a pulse information extraction unit 31 of the pulse detection circuit 30.

As shown in FIG. 1, the pulse detection circuit 30 includes the pulse information extraction unit 31, a parameter memory 32, a pulse determination unit 33, and a pulse count unit 34.

The pulse detection circuit 30 acquires the light reception level signal JS output from the disc drive 20, and analyzes a pulse signal derived from the particles 14, so as to acquire count information of the detection target substances 13. The pulse detection circuit 30 is hardware such as a dedicated circuit substrate, for example.

The pulse information extraction unit 31 extracts pulse information from a pulse included in the light reception level signal JS. The pulse information includes a pulse width and a pulse amplitude, for example. The pulse information extraction unit 31 may read out a set value of an extraction parameter stored in the parameter memory 32, and extract the pulse information included in the light reception level signal JS in accordance with the set value of the extraction parameter. For example, when the pulse width is extracted as the pulse information, the pulse information extraction unit 31 may use an extraction voltage $V_{th}$ as the extraction parameter for extracting the pulse width, and extract the pulse width at the extraction voltage $V_{th}$ as the pulse information. When the pulse amplitude is extracted as the pulse information, the pulse information extraction unit 31 may extract a peak value of the pulse as the pulse information. The extracted pulse information is output to the pulse determination unit 33.

The parameter memory 32 stores set values of pulse-related parameters including the extraction parameter and a determination parameter. The determination parameter is used for determining whether the pulse included in the light reception level signal JS is derived from the particles 14. The set value of the determination parameter in the present embodiment is a threshold. Examples of the determination parameter include an amplitude upper-limit voltage $V_H$ which is a threshold voltage of the pulse amplitude on the upper limit side, an amplitude lower-limit voltage $V_L$ which is a threshold voltage of the pulse amplitude on the lower limit side, a pulse width upper-limit time $T_H$ which is a threshold time of the pulse width on the upper limit side, and a pulse width lower-limit time $T_L$ which is a threshold time of the pulse width on the lower limit side.

The pulse determination unit 33 determines whether the pulse included in the light reception level signal JS is present within a range of a pair of thresholds including an upper-limit value and a lower-limit value set in a direction of the pulse width or in a direction of the pulse amplitude. In particular, the pulse determination unit 33 determines whether the pulse width is present within the range of the pair of thresholds regarding the pulse width, or determines whether the pulse amplitude is present within the range of the pair of thresholds regarding the pulse amplitude. The pulse determination unit 33 reads out the set value of the determination parameter from the parameter memory 32, and determines that the pulse is derived from the particles 14 when the pulse information extracted by the pulse information extraction unit 31 is within the range of the set value.

The pair of thresholds used for the determination may be se for at least either the pulse width or the pulse amplitude. For example, the pulse determination unit 33 determines that the pulse is derived from the particles 14 when the pulse width at the extraction voltage $V_{th}$ is within the range of the pulse width lower-limit time $T_L$ to the pulse width upper-limit time $T_H$. The pulse determination unit 33 also determines that the pulse is derived from the particles 14 when the pulse amplitude is within the range of the amplitude lower-limit voltage $V_L$ to the amplitude upper-limit voltage $V_H$. The pulse determination unit 33 outputs the detection signal to the pulse count unit 34 so as to increment the count value when the pulse included in the light reception level signal JS is determined to be derived from the particles 14.

The pulse count unit 34 counts the pulse present within the pair of thresholds to output the count value. In particular, the pulse count unit 34 acquires the detection signal in real time to count the pulse derived from the particles 14. The count value is output from the pulse count unit 34 to a threshold calculation unit 41 of the system controller 40, or may be output to a display unit 45 so that a user can recognize the count value. As described below, the threshold calculation unit 41 repeatedly changes at least one of the pair of thresholds by a set amount of change as a unit to generate a new pair of thresholds. The pulse determination unit 33 then counts the pulse determined to be present within the range of each pair of thresholds generated, and outputs the count value of the pulse by the amount of change at a time.

As shown in FIG. 1, the system controller 40 includes the threshold calculation unit 41, a parameter setting unit 42, a measurement controller 43, the drive controller 44, the display unit 45, and a threshold correction unit 46.

The system controller 40 controls the disc drive 20 and the pulse detection circuit 30, and executes the calculation processing and the setting regarding the count value and the determination parameter. The system controller 40 may be a computer on which a software program is installed.

Figure 6:
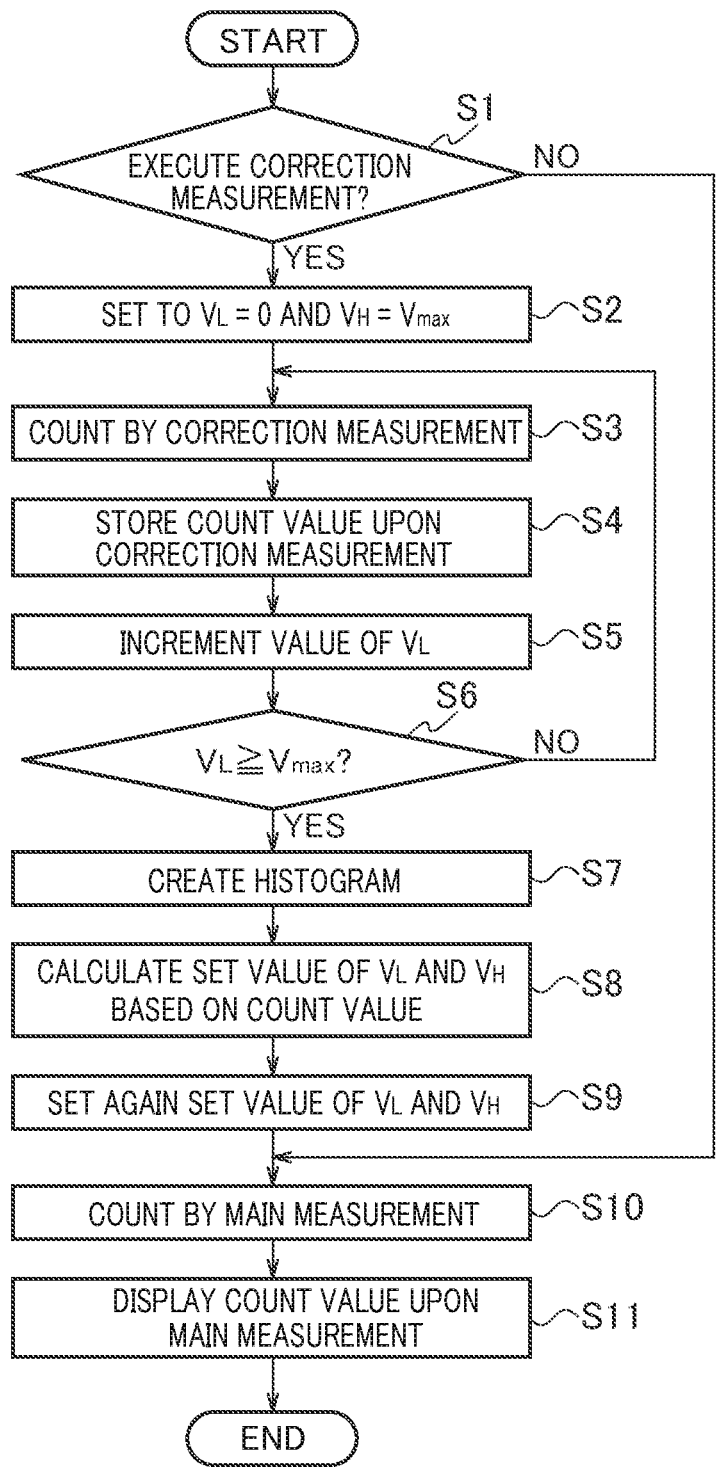
FIG. 6 is a flowchart showing an example of an analysis threshold generation method according to the first embodiment.

The threshold calculation unit 41 executes processing regarding correction measurement and main measurement as shown in the flowchart of FIG. 6 described below. The correction measurement executes the measurement for correcting the pair of thresholds according to the intensity of the irradiation light 25b and the state of the reflection characteristics of the analysis substrate 10. The main measurement executes the actual analyzation of the detection target substances 13 with the pair of thresholds corrected by the correction measurement.

The threshold calculation unit 41 outputs, to the drive controller 44, a control demand regarding the correction measurement for the movement of the optical pickup 25 and the rotation of the analysis substrate 10.

The threshold calculation unit 41 repeatedly changes at least one of the pair of thresholds by a set amount of change as a unit to generate a new pair of thresholds. In particular, the threshold calculation unit 41 generates a pair of thresholds for the pulse width of the pulse included in the light reception level signal JS, or a pair of thresholds for the pulse amplitude of the pulse. The threshold calculation unit 41 repeatedly generates a new pair of thresholds in which at least one of the pair of thresholds is changed every time the pulse count unit 34 counts the pulse until reaching a predetermined value. For example, the threshold calculation unit 41 may repeatedly change only the upper-limit or lower-limit threshold by the set amount of change as a unit to generate a new pair of thresholds. The threshold calculation unit 41 may repeatedly change the upper-limit and lower-limit thresholds by the set amount of change as a unit to generate a new pair of thresholds. When the threshold calculation unit 41 repeatedly change the upper-limit and lower-limit thresholds, both the upper-limit and lower-limit thresholds may be changed such that the gap between the upper-limit value and the lower-limit value are kept constant. The amount of change upon changing the upper-limit and lower-limit thresholds is not limited to the constant value, and may vary within a predetermined range or beyond the predetermined range, for example. As described above, the pulse count unit 34 counts the pulse determined to be present within the pair of thresholds by the pulse determination unit 33 every time the threshold calculation unit 41 generates the pair of thresholds, and outputs the count value of the pulse by the amount of change at a time.

The threshold correction unit 46 generates a pair of thresholds used for analysis in accordance with each pair of thresholds generated by the threshold calculation unit 41 and the count value output from the pulse count unit 34.

As described below, the threshold correction unit 46 may generate a frequency distribution defining each pair of thresholds generated as a class and the count value output from the pulse count unit 34 as a frequency. The threshold correction unit 46 may generate a pair of thresholds used for analysis according to the frequency distribution. The threshold correction unit 46 may also generate a pair of thresholds used for analysis in accordance with a value at a class at which the mode appears in the frequency distribution. The frequency distribution may be a histogram. The threshold correction unit 46 may generate a pair of thresholds used for analysis in accordance with an integral value of the histogram.

The parameter setting unit 42 receives the output from the threshold correction unit 46 and stores the value of the parameter to be set in the parameter memory 32.

The measurement controller 43 manages the execution of the correction measurement and the main measurement. The measurement controller 43 may include an input unit for allowing the user to choose the execution of the correction measurement or the main measurement. The measurement controller 43 may direct the drive controller 44 to execute the start, interruption, and completion of the count, or direct the threshold calculation unit 41 and the threshold correction unit 46 to execute the calculation processing, according to the information selected through the input unit.

The drive controller 44 receives the input from the measurement controller 43 to control the disc drive 20. The drive controller 44 can control a measurement position such as a measurement start position and a measurement end position of the analysis substrate 10 in the disc drive 20. The drive controller 44 may include the turntable drive circuit 44a and the optical pickup drive circuit 44b, for example.

The turntable drive circuit 44a controls the turntable drive unit 23, For example, the turntable drive circuit 44a controls the turntable drive remit 23 so as to cause the turntable 21 to rotate together with the analysis substrate 10 and the damper 22 at a constant linear velocity.

The optical pickup drive circuit 44b controls to drive the optical pickup 25. For example, the optical pickup drive circuit 44b moves the optical pickup 25 along the guide shaft 24, or moves the objective lens 25a of the optical pickup 25 in the upper-lower direction.

The drive controller 44 controls the disc drive 20 so as to repeatedly measure the same position every time at least one of the pair of thresholds is changed by the threshold calculation unit 41 during the correction measurement. For example, the drive controller 44 controls the optical pickup 25 so as to move to the measurement start position and the measurement end position, for example. To decrease the time for the correction measurement, the range of the correction measurement is preferably narrower than the range of the main measurement. In particular, the region for counting the pulse present within the range of a new pair of thresholds obtained upon the change made by the threshold calculation unit 41 is preferably narrower than the region for counting the pulse within the pair of thresholds used for analysis.

The measurement start position and the measurement end position may be preliminarily determined, or may be determined so as to obtain a predetermined count value during the correction measurement. Preliminarily determining the measurement start position and the measurement end position is preferable because the counting is only required to be repeated while at least one of the pair of thresholds is changed, which can simplify the correction. Determining the measurement start position and the measurement end position so as to obtain a predetermined count value during the correction measurement is preferable because the correction can be made with the count value of a predetermined amount or greater, which can achieve a stable correction, in such a case, the measurement start position and the measurement end position of the disc drive 20 are controlled via the threshold calculation unit 41. If the entire measurement target region measured during the main measurement is subjected to the correction measurement, it takes a lot of time. The target for the correction measurement is thus preferably assigned to substantially the middle of the measurement region for the main measurement, which is narrower than the entire measurement target region.

The display unit 45 can provide the user with the information about the correction measurement or the main measurement. An example of the information about the correction measurement is additional information such as a correction accuracy upon the correction measurement so as to allow the user to choose the subsequent processing. An example of the information about the main measurement is the count value upon the main measurement. The display unit 45 may be any device that can provide the user with the information about the correction measurement or the main measurement, and an example thereof is a display.

The respective steps in the analysis threshold generation method according to the present embodiment are described below with reference to the flowchart shown in FIG. 6. The present embodiment is illustrated below with a system in which a pulse projecting downward is generated when the particles 14 are present in a graph of which the axis of abscissas is a scanning time (a scanning position) and the axis of ordinates is a voltage. In particular, the present embodiment is illustrated with a case in which the amplitude lower-limit voltage $V_L$, the amplitude upper-limit voltage $V_H$, and the extraction voltage $V_{th}$ are each an integer proportional to the voltage within a range of 0 to +100 for illustration purposes. The present embodiment is also illustrated with the system in which a signal level in which no reflection light is detected is set to 100, and a signal level in which no particles 14 or no foreign substances are present on the analysis substrate 10 is set to a reference voltage $V_{base}$ while the signal level is set to a smaller value than the reference voltage $V_{base}$ when the particles 14 are present on the analysis substrate 10. The value of the reference voltage $V_{base}$ depends on the state of the analysis substrate 10 and the intensity of the irradiation light 25b.

The present embodiment, however, is not limited to the system described above. For example, a signal intensity (a voltage value) of the light reception level signal may be directly used, and the amplitude lower-limit voltage $V_L$, the amplitude upper-limit voltage $V_H$, and the extraction voltage $V_{th}$ may each be a decimal. In addition, the present embodiment may employ a system in which the reference voltage $V_{base}$ is zero, and a polarity of the pulse may be inverted so that the pulse projecting upward is generated when the particles 14 are present.

In step S1, the correction measurement is determined whether to be executed. The threshold calculation unit 41 leads the process to proceed to step S2 when the correction measurement is executed (YES), or leads the process to proceed to step S10 when the correction measurement is not executed (NO). The process may proceed to step S10 so as to execute only the main measurement in a case in which a long-term change such as a change over time in laser of the optical pickup 25 is only taken into consideration, since the correction measurement does not need to be executed each time. The determination of whether the correction measurement is executed may be made by the user through a graphical user interface (GUI), or may be made by the threshold calculation unit 41 according to the information about a usage period or the number of usage times.

In step S2, the threshold calculation unit 41 controls the parameter setting unit 42 so as to set the value of the amplitude lower-limit voltage $V_L$ to zero. The threshold calculation unit 41 also controls the parameter setting unit 42 so as to set the value of the amplitude upper-limit voltage $V_H$ to a value $V_{max}$ which is sufficiently greater than a preliminarily-set initial value $V_{H0}$. When the pulse width upper-limit time $T_H$ and the pulse width lower-limit time $T_L$ are used instead of the amplitude lower-limit voltage $V_L$ and the amplitude upper-limit voltage $V_H$, the threshold calculation unit 41 only needs to control the parameter setting unit 42 so as to set the extraction voltage $V_{th}$ to a preliminarily-set initial value $V_{th0}$. The threshold calculation unit 41 then leads the process to proceed to step S3.

In step S3, the threshold calculation unit 41 controls the drive controller 44 so as to count the particles 14. In particular, the threshold calculation unit 41 controls the drive controller 44 such that the optical pickup 25 is caused to move in the radial direction of the analysis substrate 10 from the measurement start position to the measurement end position for the correction measurement, or such that the analysis substrate 10 is caused to rotate at a regular speed.

The count of the particles 14 is execute by the pulse detection circuit 30. The optical pickup 25 irradiates, with the irradiation light 25b, the surface of the analysis substrate 10 to which the detection target substances 13 and the particles 14 bound to the detection target substances 13 are fixed (an irradiation step), The optical pickup 25 receives the reflection light of the irradiation light 25b from the analysis substrate 10 to generate the light reception level signal JS (a signal generation step). The pulse information of the pulse included in the light reception level signal JS generated is acquired by the pulse information extraction unit 31. The pulse determination unit 33 determines whether the pulse included in the light reception level signal JS is present within the pair of thresholds set for the pulse width, or whether the pulse included in the light reception level signal JS is present within the pair of thresholds set for the pulse amplitude (a determination step). The pulse determination unit 33 outputs the detection signal to the pulse count unit 34 so as to increment the count value when determining that the pulse included in the light reception level signal JS is present within the pair of thresholds. The pulse count unit 34 counts the pulse present within the pair of thresholds to output the count value to the threshold calculation unit 41. Namely, the pulse count unit 34 counts the pulse determined to be present within the set paired thresholds in the determination step, and outputs the count value of the pulse counted (a count value output step). The process then proceeds to step S4.

In step S4, the threshold calculation unit 41 stores, in the count table, the count value of the particles 14 acquired upon the correction measurement in step S3 and associated with the value of the set amplitude lower-limit voltage $V_L$. The process then proceeds to step S5.

In step S5, the threshold calculation unit 41 controls the parameter setting unit 42 so as to set again the amplitude lower-limit voltage $V_L$ stored in the parameter memory 32 with the incremented value. For example, when the value of the set amplitude lower-limit voltage $V_L$ is $V_{Ln}$, the threshold calculation unit 41 notifies the parameter setting unit 42 so as to increment the value $V_{Ln}$ to lead the amplitude lower-limit voltage $V_L$ to $V_{Ln}+1=V_{Ln+1}$ (n is an integer of zero or greater and smaller than $V_{max}$). While the present embodiment is illustrated with the case in which the threshold calculation unit 41 adds 1 to the original amplitude lower-limit voltage $V_L$, the value to be added is not limited to 1. The threshold calculation unit 41 then leads the process to proceed to step S6.

In step S6, the threshold calculation unit 41 determines whether the set value of the amplitude lower-limit voltage $V_L$ is $V_{max}$ or greater. The threshold calculation unit 41 leads the process to proceed to step S3 when the set value of the amplitude lower-limit voltage $V_L$ is smaller than $V_{max}$ (NO), or leads the process to proceed to step S7 when the set value of the amplitude lower-limit voltage $V_L$ is $V_{max}$ or greater (YES).

Through the process from step S3 to step S6, the threshold calculation unit 41 repeatedly generates anew pair of thresholds in which at least one of the pair of thresholds is changed every time the pulse count unit 34 counts the pulse in the count value output step until reaching a predetermined value (a first threshold generation step). In particular, the threshold calculation unit 41 repeatedly adds 1 to the amplitude lower-limit voltage $V_L$ to change the value to a series of different values, namely, new pairs of thresholds, so as to obtain plural values for the amplitude lower-limit voltage $V_L$. When the set value of the amplitude lower-limit voltage $V_L$ is counted from zero to $V_{max}$, the count table is completed, as shown in FIG. 7, for example.

The count table shown in FIG. 7 stores the plural thresholds in the left column, and stores the count values counted for each pair of thresholds changed and obtained. In particular, the count table stores the count value Count $(v_n)$ associated with each set value $V_n$ of the amplitude lower-limit voltage $V_L$. The respective count values when set from $V_L=0$ to $V_L=V_{max}$ are stored in the count table as Count (0) to Count $(V_{max})$. The count value Count $(v_n)$ is the count value when the set value of the amplitude lower-limit voltage $V_L$ is $V_n$ (n is an integer of zero to $V_{max}$).

In step S7, the pulse count unit 34 counts the pulse determined to be present within each pair of thresholds of the respective paired thresholds by the pulse determination unit 33, and outputs the count value of the pulse by the amount of change at a time. In the present embodiment, the count value of the pulse by the amount of change at a time is given by dCount $(v_n)$ according to the following mathematical formula (1):

$$dCount(v_n) = Count(v_n) - Count(v_{n+1}) \qquad (1)$$

Figure 8:
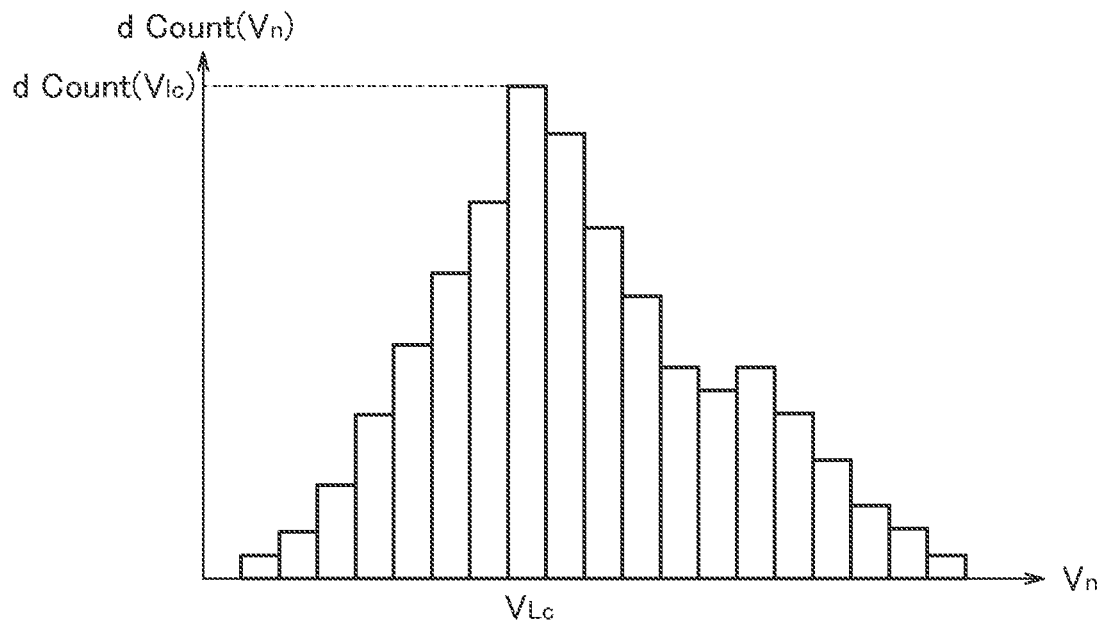
FIG. 8 is a diagram for explaining a method of calculating a pair of thresholds according to the mode of a histogram.

The threshold correction unit 46 generates the frequency distribution defining each pair of thresholds as a class and the count value output from the pulse count unit 34 as a frequency. The present embodiment uses the frequency distribution which is a histogram in which the amplitude lower-limit voltage $V_L$ is set as a class and dCount ($v_n$) is set as a frequency so as to make a graph from $V_L$=zero to $V_L$=$V_{max}$ to obtain the histogram as shown in FIG. 8, The threshold correction unit 46 leads the process to proceed to step S8.

In step S8, the threshold correction unit 46 generates a pair of thresholds used for analysis according to each pair of thresholds generated in the first threshold generation step and the count value output in the count value output step (a second threshold generation step). The threshold correction unit 46 may generate a pair of thresholds used for analysis according to the frequency distribution. In the present embodiment, the threshold correction unit 46 generates the appropriate amplitude lower-limit voltage $V_L$ and amplitude upper-limit voltage $V_H$ according to the histogram.

The threshold correction unit 46 may generate a pair of thresholds used for analysis according to a value at a class at which the mode appears in the frequency distribution. FIG. 8 illustrates the case in which the frequency distribution is the histogram. When a value at a class is defined as a voltage $V_{Lc}$ in a case in which a value at a frequency at which the mode appears in the histogram is dCount ($v_{Lc}$), the voltage $V_{Lc}$ is presumed to be a measure of central tendency of the amplitude of the pulse signal derived from the particles 14. In other words, the voltage $V_{Lc}$ is presumed to be a parameter substantially proportional to the intensity of the light emitted to the analysis substrate 10 and the intensity of the signal in which the reflection characteristics of the analysis substrate 10 and the particles 14, for example, are taken into consideration. The amplitude lower-limit voltage $V_L$ and the amplitude upper-limit voltage $V_H$ thus can be corrected in accordance with the voltage $V_{Lc}$ obtained. Similarly, the extraction voltage $V_{th}$ can also be corrected in accordance with the voltage $V_{Lc}$ obtained. In particular, a correction value of each parameter can be calculated according to the following mathematical formula (2), mathematical formula (3), and mathematical formula (4) based on an initial value upon shipping:

$$V_{La} = V_{Li}(V_{Lcp}/V_{Lci}) \qquad (2)$$

$$V_{Ha} = V_{Hi}(V_{Lcp}/V_{Lci}) \qquad (3)$$

$$V_{tha} = V_{thi}(V_{Lcp}/V_{Lci}) \qquad (4)$$

In the mathematical formula (2), the mathematical formula (3), and the mathematical formula (4), $V_{Li}$, $V_{Hi}$, $V_{thi}$, and $V_{Lci}$ are initial values of the amplitude lower-limit voltage $V_L$, the amplitude upper-limit voltage $V_H$, the extraction voltage $V_{th}$, and the voltage $V_{Lc}$, upon shipping. In the mathematical formula (2), the mathematical formula (3), and the mathematical formula (4), $V_{Lcp}$ is a value of the voltage $V_{Lc}$ led from the histogram. In the mathematical formula (2), the mathematical formula (3), and the mathematical formula (4), $V_{La}$, $V_{Ha}$, and $V_{tha}$ are correction values of the amplitude lower-limit voltage $V_L$, the amplitude upper-limit voltage $V_H$, and the extraction voltage $V_{th}$ calculated by the correction measurement.

Another method could be presumed that branches the irradiation light 25b toward the analysis substrate 10 into a light for irradiation and a light for luminous intensity measurement, and corrects pulse determination conditions depending on the measurement value of the luminous intensity. This method, however, cannot take account of variation in the optical characteristics of the analysis substrate 10 or the particles 14. This method further needs to build up an optical system and a measurement system for measuring the luminous intensity before irradiating the analysis substrate 10 with the irradiation light 25b. This method thus needs to add hardware to the disc drive 20, which may lead to a complication in structure, an increase in cost, and a reduction in flexibility of choice of the disc drive 20 itself. In contrast, the analysis threshold generation device 100 and the analysis threshold generation method according to the present embodiment can generate the pair of thresholds while taking account of the intensity of the light emitted to the analysis substrate 10 and the reflection characteristics of the analysis substrate 10 and the particles 14.

Figure 9:
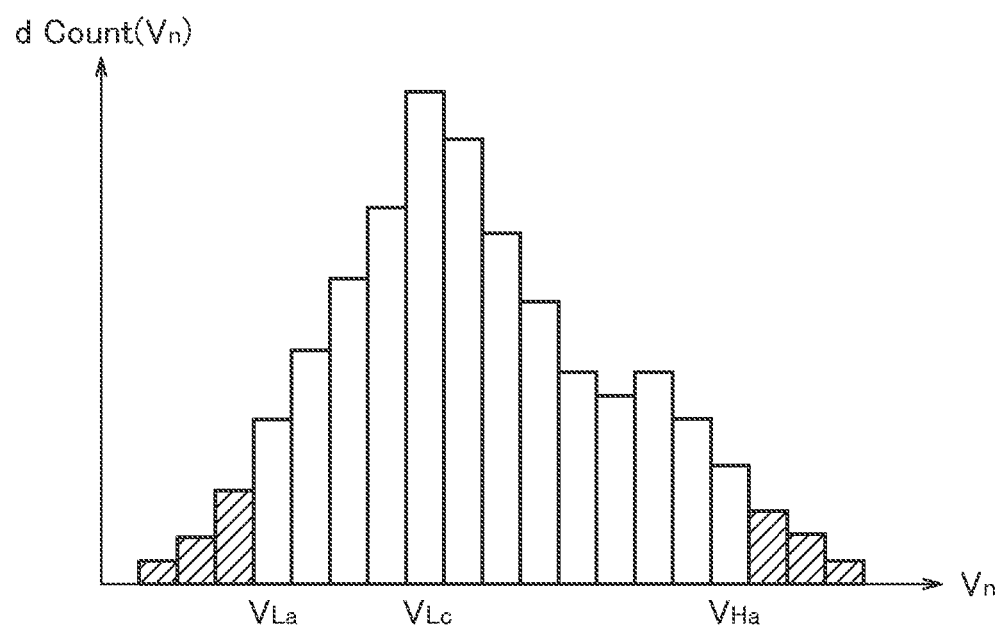
FIG. 9 is a diagram for explaining a method of calculating a pair of thresholds according to an integral value of a histogram.

Alternatively, as shown in FIG. 9, the threshold correction unit 46 may generate a pair of thresholds used for analysis according to an integral value of a histogram. In particular, as indicated by the shaded parts in the obtained histogram shown in FIG. 9, a frequency at which an integral value (an area) on each of the upper limit side and the lower limit side is a predetermined ratio or smaller of the entire integral value (the entire area) may be determined to be the amplitude lower-limit voltage $V_{La}$ and the amplitude upper-limit voltage $V_{Ha}$. In this case, the pair of thresholds can be corrected according to the predetermined ratio as described above regardless of whether the histogram is not a normal distribution or the voltage $V_{Lc}$ is shifted from the middle of the histogram, so as to achieve the stable main measurement. The predetermined ratio may be determined as appropriate, and may be set in a range of 5% to 10%.

When the extraction voltage $V_{th}$ is set to a full width at half maximum of the pulse amplitude, a correction value of each parameter may be calculated according to the following mathematical formula (5):

$$V_{th} = (V_{base} - V_{Lcp})/2 \qquad (5)$$

In the mathematical formula (5), $V_{Lcp}$ is a value of the voltage $V_{Lc}$ obtained according to the histogram, and $V_{base}$ is a value of the reference voltage described above.

In step S9, the threshold correction unit 46 controls the parameter setting unit 42 so as to set again the amplitude upper-limit voltage $V_H$ and the amplitude lower-limit voltage $V_L$ generated according to the count table as a pair of thresholds used for analysis. The threshold correction unit 46 then leads the process to proceed to step S10.

In step S10, the threshold correction unit 46 controls the drive controller 44 so as to count the particles 14 upon the main measurement with the pair of thresholds used for analysis. In particular, the threshold correction unit 46 controls the drive controller 44 such that the optical pickup 25 is caused to move in the radial direction of the analysis substrate 10 from the measurement start position to the measurement end position for the main measurement, or such that the analysis substrate 10 is caused to rotate at a regular speed.

The drive controller 44 controls the disc drive 20, subjects the analysis substrate 10 to the main measurement from the measurement start position to the measurement end position set for the main measurement, and causes the pulse detection circuit 30 to count the pulse derived from the particles 14. The count of the particles 14 is executed by the pulse detection circuit 30 in the same manner as in step S3, excluding the count with the pair of thresholds used for analysis. The threshold correction unit 46 then leads the process to proceed to step S11.

In step S11, the count value upon the main measurement is displayed on the display unit 45, and the main measurement thus ends.

The embodiment has been illustrated above with the case of repeatedly changing one of the pair of thresholds by the set amount of change as a unit, but may repeatedly change both of the pair of thresholds by the set amount of change as a unit. For example, the process may be executed such that the amplitude lower-limit voltage $V_L$ is set to 0 and the amplitude upper-limit voltage $V_H$ is set to 1 in step S2 to increment these voltages to lead $V_L$ to $V_n+1=V_{Ln+1}$ and lead $V_H$ to $V_{Ln+1}+1=V_{Ln+2}$ in step S5 so as to directly obtain the distribution corresponding to dCount ($v_n$). In this case, the condition for completing the correction measurement in step S6 may be set to be a point at which the set value of $V_H$ is led to $V_{max}$.

The embodiment has been illustrated above with the method of counting the pulse while changing the amplitude lower-limit voltage $V_L$ or the amplitude upper-limit voltage $V_H$ to correct the amplitude lower-limit voltage $V_L$ and the amplitude upper-limit voltage $V_H$. The pulse amplitude and the pulse width are proportional to each other when the pulse waveform is presumed to be a normal distribution. Replacing the amplitude lower-limit voltage $V_L$ with the pulse width lower-limit time $T_L$ and replacing the amplitude upper-limit voltage $V_H$ with the pulse width upper-limit time $T_H$ to execute the same measurement, can also achieve the same effects.

As described above, the analysis threshold generation device 100 according to the present embodiment includes the optical pickup 25 for irradiating the analysis substrate 10 with the irradiation light 25b and receiving the reflection light of the irradiation light 25b from the analysis substrate 10 so as to generate the light reception level signal JS. The detection target substances 13 and the particles 14 bound to the detection target substances 13 are fixed to the surface of the analysis substrate 10. The analysis threshold generation device 100 includes the threshold calculation unit 41 for generating a pair of thresholds for the pulse width of the pulse included in the light reception level signal JS or a pair of thresholds for the pulse amplitude of the pulse. The analysis threshold generation device 100 includes the pulse determination unit 33 for determining whether the pulse width is present within the range of the pair of thresholds for the pulse width or determining whether the pulse amplitude is present within the range of the pair of thresholds for the pulse amplitude. The analysis threshold generation device 100 includes the pulse count unit 34 for counting the pulse determined to be present within the range of the generated paired thresholds by the pulse determination unit 33 and outputting the count value of the pulse counted. The analysis threshold generation device 100 includes the threshold correction unit 46 for generating a pair of thresholds used for analysis in accordance with the pair of thresholds generated by the threshold calculation unit 41 and the count value output from the pulse count unit 34. The threshold calculation unit 41 repeatedly generates a new pair of thresholds in which at least one of the pair of thresholds is changed every time the pulse count unit 34 counts the pulse until reaching a predetermined value.

The analysis threshold generation method according to the present embodiment includes an irradiation step of irradiating, with the irradiation light 25b, the surface of the analysis substrate 10 to which the detection target substances 13 and the particles 14 bound to the detection target substances 13 are fixed. The analysis threshold generation method includes a signal generation step of receiving the reflection light of the irradiation light 25b from the analysis substrate 10 to generate the light reception level signal JS. The analysis threshold generation method includes a determination step of determining whether the pulse included in the light reception level signal JS is present within the range of the pair of thresholds set for the pulse width or determining whether the pulse is present within the range of the pair of thresholds set for the pulse amplitude. The analysis threshold generation method includes a count value output step of counting the pulse determined to be present within the set paired thresholds in the determination step, and outputting the count value of the pulse counted. The analysis threshold generation method includes a first threshold generation step of repeatedly generating a new pair of thresholds in which at least one of the pair of thresholds is changed every time the pulse is counted in the count value output step until reaching a predetermined value. The analysis threshold generation method includes a second threshold generation step of generating a pair of thresholds used for analysis in accordance with each pair of thresholds generated and the count value output in the count value output step.

The analysis threshold generation device 100 and the analysis threshold generation method can correct the determination parameter to detect the pulse regardless of a change in the irradiation intensity of light toward the analysis substrate 10 from the optical pickup 25 or a change in the reflection characteristics of the analysis substrate 10 and the particles 14. The analysis threshold generation device 100 and the analysis threshold generation method according to the present embodiment thus can count the detection target substances 13 regardless of the conditions upon counting the particles.

Second Embodiment

An analysis threshold generation device 100 and an analysis threshold generation method according to a second embodiment are described in detail below. The same elements as in the first embodiment are denoted by the same reference numerals, and overlapping explanations are not repeated below.

Figure 10:
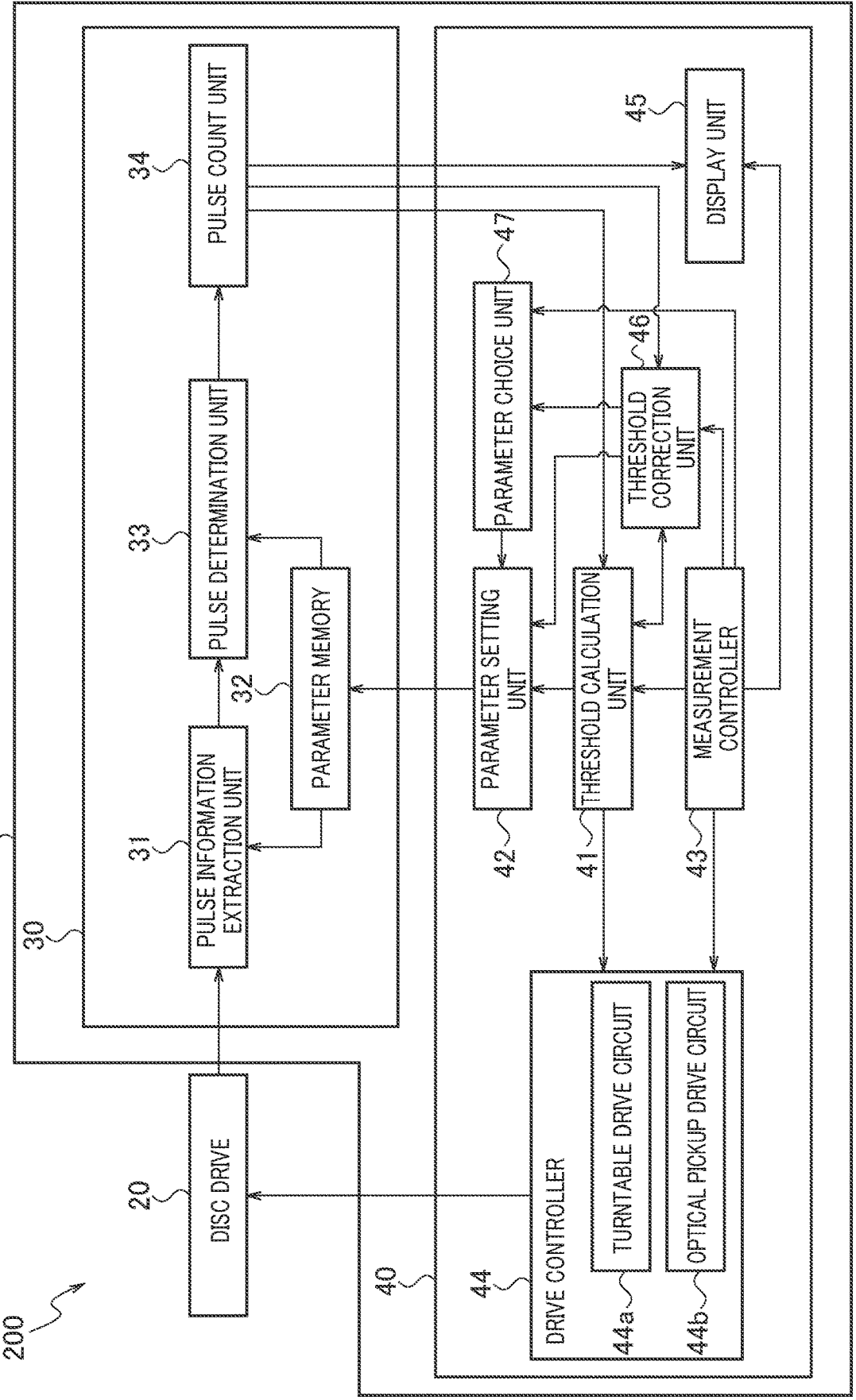
FIG. 10 is a block diagram showing a configuration of an analysis threshold generation device according to a second embodiment.

As shown in FIG. 10, the analysis threshold generation device 100 according to the present embodiment further includes a parameter choice unit 47.

The parameter choice unit 47 is a memory for storing a pair of thresholds used for analysis generated by the threshold correction unit 46 and associated with an analysis condition. The threshold correction unit 46 causes the pair of thresholds used for analysis to be associated with the analysis condition and stored in the memory. The pair of thresholds used for analysis can also be corrected thresholds. The corrected paired thresholds associated with the analysis condition and stored may be chosen by the user via the measurement controller 43 depending on the analysis condition. The parameter choice unit 47 outputs the corrected paired thresholds corresponding to the analysis condition to the parameter setting unit 42 according to a direction by the measurement controller 43, and stores the pair of thresholds in the parameter memory 32 via the parameter setting unit 42. Presuming that substantially the same histogram is obtained when the analysis condition used is the same, choosing a pulse-related parameter depending on the analysis condition can eliminate the necessity of executing the correction measurement for every main measurement.

The analysis condition varies depending on the analysis substrate 10 and the disc drive 20, for example. Examples of cases of varying depending on the analysis substrate 10 include a case of changing the type and the surface condition of the analysis substrate 10, a case of changing a method of fixing the particles 14 to the analysis substrate 10, a case of changing a reagent used for fixing the particles 14, a case of changing the type of the particles 14, and a case of changing a manufacturing lot of the particles 14. Examples of cases of varying depending on the disc drive 20 include a case of changing the type of the disc drive 20, a case of changing a loading speed of the disc drive 20, and a case of changing a method of controlling laser power. The analysis condition may be stored with a name assigned such as a disc assay protocol 1 and a disc assay protocol 2, for example.

Figure 11:
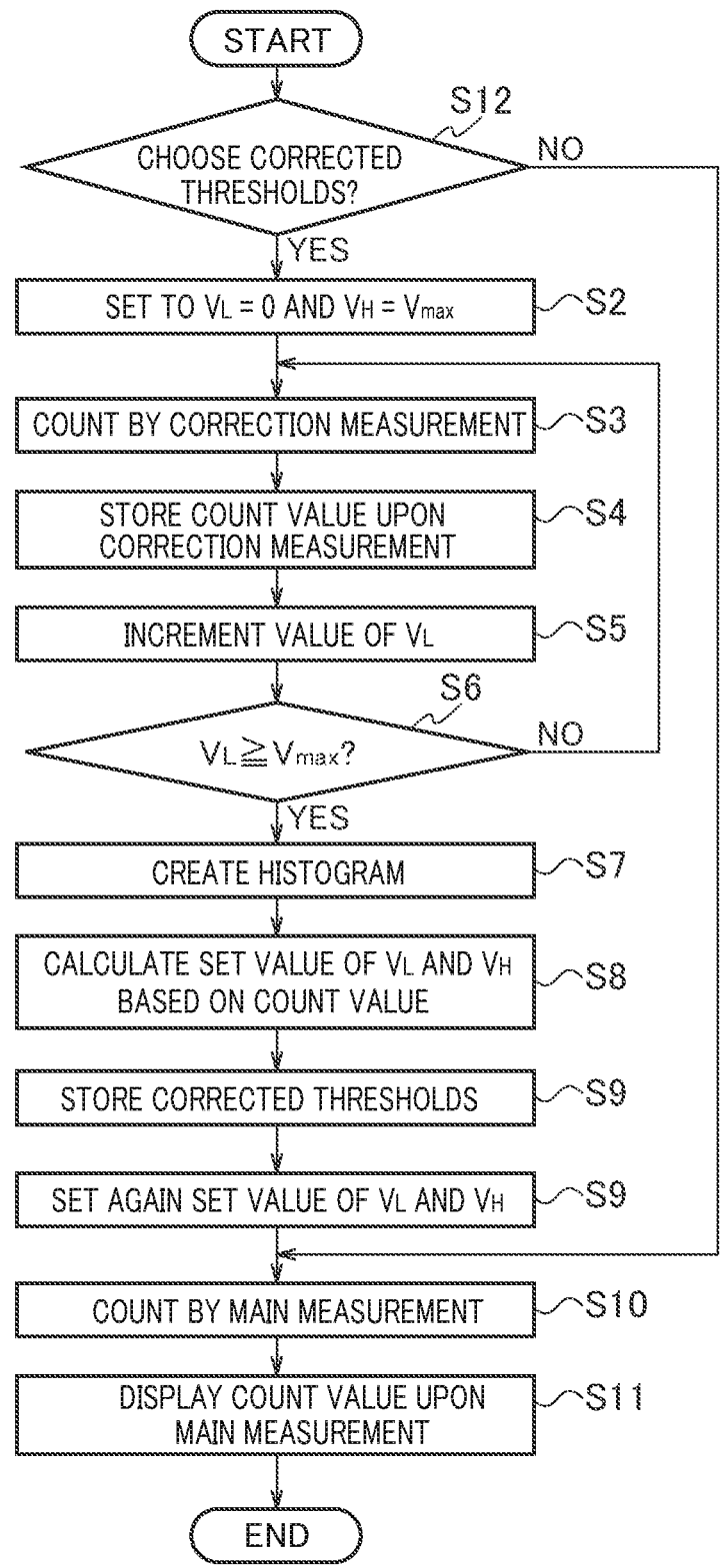
FIG. 11 is a flowchart showing an example of an analysis threshold generation method according to the second embodiment.

The respective steps in the analysis threshold generation method according to the present embodiment are described below with reference to the flowchart shown in FIG. 11. The process from step S1 to step S11 is the same as in the first embodiment, and overlapping explanations are not repeated below.

In step S12, the user, for example, determines whether to choose the corrected paired thresholds stored in the parameter choice unit 47. When a pair of thresholds having been corrected before by the correction measurement under the same condition is stored, the user and the like chooses the corrected paired thresholds stored in the parameter choice unit 47 without executing the correction measurement again (YES), and the process proceeds to step S10. When the user wants to try a new condition and redo the correction measurement, the user does not choose the corrected paired thresholds (NO), and the same processing as in step S2 to step S8 is executed, and the process then proceeds to step S13.

In step S13, the corrected paired thresholds generated by the correction measurement in step S2 to step S8 are associated with the analysis condition and stored in the parameter choice unit 47. Storing the corrected paired thresholds in the parameter choice unit 47 can execute the main measurement, without the correction measurement, while only choosing the corrected paired thresholds stored with substantially the same accuracy as in the case of executing the correction measurement.

The analysis threshold generation device 100 and the analysis threshold generation method according to the present embodiment can choose the corrected paired thresholds appropriate for every analysis condition regardless of whether the analysis conditions differ from the respective cases. The analysis threshold generation device 100 and the analysis threshold generation method according to the present embodiment thus can count the detection target substances 13 regardless of the conditions upon counting the particles.

The entire content of Japanese Patent Application No. P2018-408514 (filed on Jun. 6, 2018) is herein incorporated by reference.

While the present embodiments have been described above by reference to the examples, it should be understood that the present embodiments are not intended to be limited to the descriptions above, and various modifications and improvements will be apparent to those skilled in the art.

The present discloser can provide the analysis threshold generation device and the analysis threshold generation method capable of counting the detection target substances regardless of the conditions upon counting the particles.

What is claimed is:

1. An analysis threshold generation device comprising:
    an optical pickup configured to irradiate, with an irradiation light, an analysis substrate of an optical disc, the analysis substrate of the optical disc having a surface to which a detection target substance and a particle bound to the detection target substance are fixed, and receive a reflection light of the irradiation light from the analysis substrate to generate a light reception level signal;
    a threshold calculation unit configured to generate a pair of thresholds for a pulse width of a pulse included in the light reception level signal or a pair of thresholds for a pulse amplitude of the pulse, the pair of thresholds for the pulse width including a pulse width upper-limit time which is a threshold time of the pulse width on an upper limit side and a pulse width lower-limit time which is a threshold time of the pulse width on a lower limit side, and the pair of thresholds for the pulse amplitude including an amplitude upper-limit voltage which is a threshold voltage of the pulse amplitude on an upper limit side and an amplitude lower-limit voltage which is a threshold voltage of the pulse amplitude on a lower limit side;
    a pulse determination unit configured to determine whether the pulse width is present within a range of the pair of thresholds for the pulse width or determine whether the pulse amplitude is present within a range of the pair of thresholds for the pulse amplitude;
    a pulse count unit configured to count the pulse determined to be present within the range of the generated pair of thresholds by the pulse determination unit, and output a count value of the pulse counted;
    a threshold correction unit configured to generate a pair of thresholds used for analysis in accordance with the pair of thresholds generated by the threshold calculation unit and the count value output from the pulse count unit; and
    a drive controller configured to control a position of the optical pickup so as to repeatedly measure a same position every time at least one of the pair of thresholds is changed by the threshold calculation unit,
    wherein the drive controller is configured to control the optical pickup so as to move the optical pickup to a measurement start position in order to repeatedly measure the same position every time at least one of the pair of thresholds is changed by the threshold calculation unit, and
    wherein the threshold calculation unit is configured to repeatedly generate a new pair of thresholds in which at least one of the pair of thresholds is changed every time the pulse count unit counts the pulse until reaching a predetermined value.

2. The analysis threshold generation device according to claim 1, wherein the threshold correction unit generates the pair of thresholds used for analysis according to a frequency distribution in which each pair of thresholds generated is defined as a class and the count value output from the pulse count unit is defined as a frequency.

3. The analysis threshold generation device according to claim 2, wherein the threshold correction unit generates the pair of thresholds used for analysis in accordance with a value at a class at which a mode appears in the frequency distribution.

4. The analysis threshold generation device according to claim 2, wherein the frequency distribution is a histogram, and the threshold correction unit generates the pair of thresholds used for analysis in accordance with an integral value of the histogram.

5. The analysis threshold generation device according to claim 1, wherein the threshold correction unit stores the pair of thresholds used for analysis to be associated with an analysis condition in a memory.

6. An analysis threshold generation method comprising:
an irradiation step of irradiating, with an irradiation light, an analysis substrate of an optical disc, the analysis substrate of the optical disc having a surface to which a detection target substance and a particle bound to the detection target substance are fixed;
a signal generation step of receiving a reflection light of the irradiation light from the analysis substrate to generate a light reception level signal;
a determination step of determining whether a pulse included in the light reception level signal is present within a range of a pair of thresholds set for a pulse width or determining whether the pulse is present within a range of a pair of thresholds set for a pulse amplitude, the pair of thresholds set for the pulse width including a pulse width upper-limit time which is a threshold time of the pulse width on an upper limit side and a pulse width lower-limit time which is a threshold time of the pulse width on a lower limit side, and the pair of thresholds set for the pulse amplitude including an amplitude upper-limit voltage which is a threshold voltage of the pulse amplitude on an upper limit side and an amplitude lower-limit voltage which is a threshold voltage of the pulse amplitude on a lower limit side;
a count value output step of counting the pulse determined to be present within the range of the set pair of thresholds in the determination step, and outputting a count value of the pulse counted;
a first threshold generation step of repeatedly generating a new pair of thresholds in which at least one of the pair of thresholds is changed every time the count value output step counts the pulse until reaching a predetermined value,
wherein and a position of an optical pickup configured to irradiate the analysis substrate with the irradiation light is controlled so as to repeatedly measure a same position every time at least one of the pair of thresholds is changed, and
wherein the optical pickup is controlled so as to move to a measurement start position in order to repeatedly measure the same position every time at least one of the pair of thresholds is changed; and
a second threshold generation step of generating a pair of thresholds used for analysis in accordance with each pair of thresholds generated and the count value output in the count value output step.

* * * * *